(12) United States Patent
Chi et al.

(10) Patent No.: US 9,219,237 B1
(45) Date of Patent: Dec. 22, 2015

(54) HETEROLEPTIC IR(III) PHOSPHORS WITH BIS-TRIDENTATE CHELATING ARCHITECTURE FOR HIGH EFFICIENCY OLEDS

(71) Applicant: NATIONAL TSING HUA UNIVERSITY, Hsinchu (TW)

(72) Inventors: Yun Chi, Hsinchu (TW); Bi-Hai Tong, Ma'anshan (CN); Tai-Nan Duan, Chongqing (CN); Hsiao-Yun Ku, Hsinchu (TW); I-Jen Chen, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 14/660,156

(22) Filed: Mar. 17, 2015

(30) Foreign Application Priority Data

Dec. 23, 2014 (TW) .................. 103144964

(51) Int. Cl.
  *C07F 15/00* (2006.01)
  *H01L 51/00* (2006.01)
(52) U.S. Cl.
  CPC ........ *H01L 51/0085* (2013.01); *C07F 15/0033* (2013.01)
(58) Field of Classification Search
  USPC ...................................... 546/2, 10
  See application file for complete search history.

(56) References Cited

U.S. PATENT DOCUMENTS 8,580,961 B2   11/2013  Chi et al.

OTHER PUBLICATIONS

Tong, B. et al.: Heteroleptic Ir(III) phosphors with bis-tridentate chelating architecture for high efficiency OLEDs. J. of Materials Chemistry C, vol. 3, pp. 3460-3471, 2015.*
Wilkinson et al., "Luminescent Complexes of Iridium(III) Containing NCN-Coordinating Terdentate Ligands", Inorganic Chemistry, 2006, vol. 45, No. 21, pp. 8685-8699.

* cited by examiner

*Primary Examiner* — Charanjit Aulakh
(74) *Attorney, Agent, or Firm* — Birch, Stewart, Kolasch & Birch, LLP

(57) ABSTRACT

A bis-tridentate iridium complex represented by a formula (I):

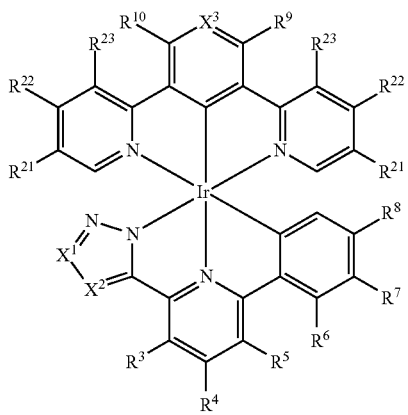

where $R^3$ to $R^8$, $R^{21}$ to $R^{23}$, $R^9$, $R^{10}$, $X^1$, $X^2$, and $X^3$ are as defined in the specification.

10 Claims, No Drawings

HETEROLEPTIC IR(III) PHOSPHORS WITH BIS-TRIDENTATE CHELATING ARCHITECTURE FOR HIGH EFFICIENCY OLEDS

CROSS-REFERENCE TO RELATED APPLICATION

This application claims priority from Taiwanese application no. 103144964, filed on Dec. 23, 2014, the disclosure of which is incorporated in its entirety herein by reference.

FIELD

The disclosure relates to iridium complexes, more particularly to bis-tridentate iridium (III) complexes.

BACKGROUND

Andrew J. Wilkinson et al disclose luminescent complexes, in an article entitled, "Luminescent Complexes of Iridium (III) Containing N^C^N-Coordinating Terdentate Ligands," published in Inorganic Chemistry vol. 45, no. 21, 2006, p8685-8699. The luminescent complexes include two bis-tridentate iridium complexes (i.e., complexes 3 and 4 shown in Scheme 5 of the article). As disclosed on page 8690, from line 30 of the left column to line 3 of the right column, the yields of the complexes 3 and 4 are 37% and 21%, respectively, which are relatively low. Thus, the complexes 3 and 4 are not suitable for use as a material for making organic light-emitting diodes (OLEDs).

SUMMARY

Therefore, an object of the disclosure is to provide a series of bis-tridentate iridium (III) complexes in higher synthetic yields, with better control of emission color and higher emission efficiencies, which are advantageous in OLED fabrication processes.

According to the disclosure, a class of bis-tridentate iridium (III) complexes is represented by a formula (I):

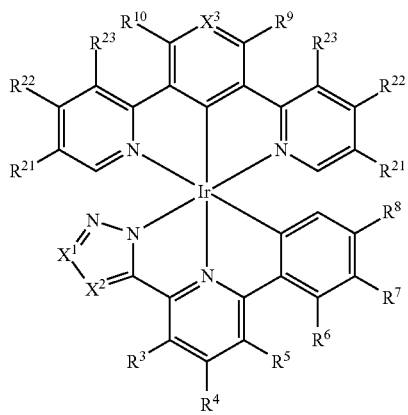

(I)

where:

$R^3$ to $R^8$ are each independently a hydrogen atom, a fluorine atom, an alkyl group, a perfluoroalkyl group, an alkoxy group, an aryl group, a dimethylamino group, a diphenylamino group, or a carbazolyl group;

$R^{21}$ to $R^{23}$ are each independently a hydrogen atom, a fluorine atom, an alkyl group, a perfluoroalkyl group, an alkoxy group, an aryl group, a dimethylamino group, a diphenylamino group, or a carbazolyl group, or $R^{21}$ and $R^{22}$ or $R^{22}$ and $R^{23}$ are alkene groups joined to form a benzene ring which may be substituted by a fluorine atom, an alkyl group, a perfluoroalkyl group, an alkoxy group, an aryl group, a dimethylamino group, a diphenylamino group, or a carbazolyl group;

$R^9$ and $R^{10}$ are each independently a hydrogen atom, a fluorine atom, or an alkoxy group;

$X^1$ is a nitrogen atom or $C-X^{11}$, $X^{11}$ being a perfluoroalkyl group;

$X^2$ is a nitrogen atom or CH; and $X^3$ is a nitrogen atom or $C-X^{31}$, $X^{31}$ being a hydrogen atom, a fluorine atom, a cyano group, an alkyl group, a perfluoroalkyl group, an alkoxy group, or an aryl group.

DETAILED DESCRIPTION

A bis-tridentate iridium (III) complex according to the disclosure is represented by a formula (I):

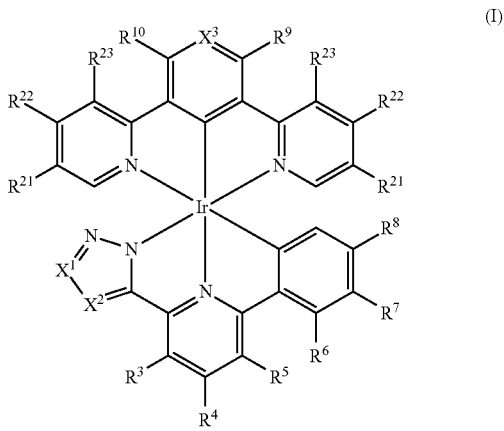

(I)

where:

$R^3$ to $R^8$ are each independently a hydrogen atom, a fluorine atom, an alkyl group, a perfluoroalkyl group, an alkoxy group, an aryl group, a dimethylamino group, a diphenylamino group, or a carbazolyl group;

$R^{21}$ to $R^{23}$ are each independently a hydrogen atom, a fluorine atom, an alkyl group, a perfluoroalkyl group, an alkoxy group, an aryl group, a dimethylamino group, a diphenylamino group, or a carbazolyl group, or $R^{21}$ and $R^{22}$ or $R^{22}$ and $R^{23}$ are alkene groups joined to form a benzene ring which may be substituted by a fluorine atom, an alkyl group, a perfluoroalkyl group, an alkoxy group, an aryl group, a dimethylamino group, a diphenylamino group, or a carbazolyl group;

$R^9$ and $R^{10}$ are each independently a hydrogen atom, a fluorine atom, or an alkoxy group;

$X^1$ is a nitrogen atom or $C-X^{11}$, $X^{11}$ being a perfluoroalkyl group;

$X^2$ is a nitrogen atom or CH; and $X^3$ is a nitrogen atom or $C-X^{31}$, $X^{31}$ being a hydrogen atom, a fluorine atom, a cyano group, an alkyl group, a perfluoroalkyl group, an alkoxy group, or an aryl group.

In this specification, for example, the alkyl group is C1 to C6 alkyl, the perfluoroalkyl group is C1 to C6 perfluoroalkyl, the alkoxy group is C1 to C6 alkoxy, and the aryl group is C6 to C10 aryl such as phenyl or naphthyl.

Preferably, $X^1$ is C—$X^{11}$, and $X^{11}$ is a perfluoroalkyl group. More preferably, $X^{11}$ is $CF_3$.

Preferably, $X^2$ is CH.

Preferably, $X^3$ is C—$X^{31}$, and $X^{31}$ is a hydrogen atom, a fluorine atom, a cyano group, an alkyl group, a perfluoroalkyl group, an alkoxy group, or an aryl group. More preferably, $X^{31}$ is a hydrogen atom or an alkyl group. In one example of the bis-tridentate iridium complex, $X^{31}$ is a hydrogen atom, and $R^9$ and $R^{10}$ are each a fluorine atom. In another example of the bis-tridentate iridium complex, $X^{31}$ is an alkyl group, and $R^9$ and $R^{10}$ are each a hydrogen atom.

Preferably, $R^3$, $R^4$, $R^5$, $R^6$, and $R^7$ are each a hydrogen atom, and $R^8$ is an alkyl group or a perfluoroalkyl group.

In one example of the bis-tridentate iridium complex, $R^{21}$ to $R^{23}$ are each independently a hydrogen atom or an alkyl group. In another example of the bis-tridentate iridium complex, $R^{21}$ is a hydrogen atom or an alkyl group, and $R^{22}$ and $R^{23}$ are alkene groups joined to form a benzene ring which may be alkyl substituted.

Preferably, the bis-tridentate iridium complex is

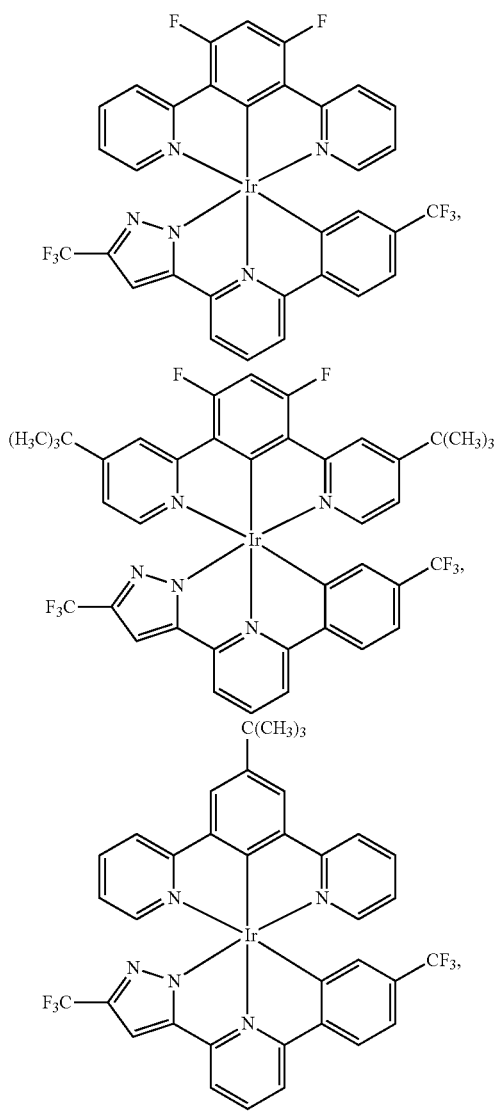

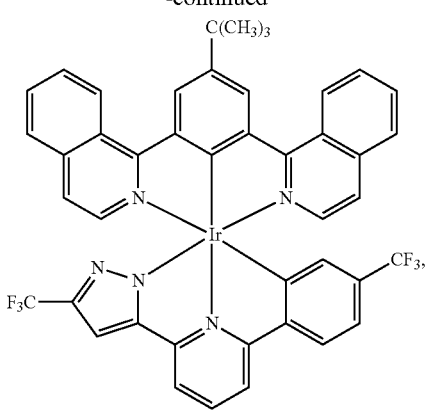

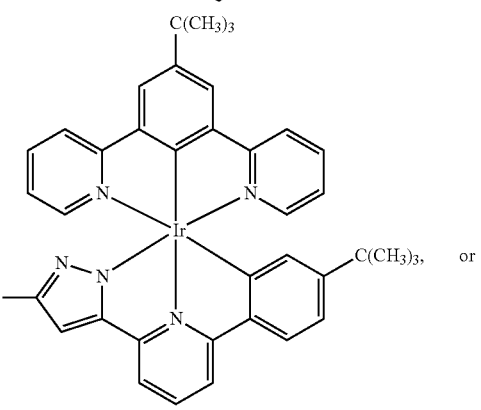

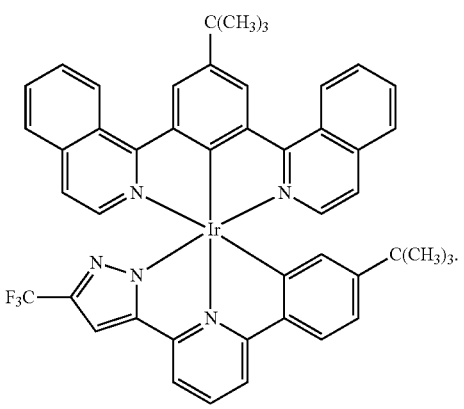

More preferably, the bis-tridentate iridium complex

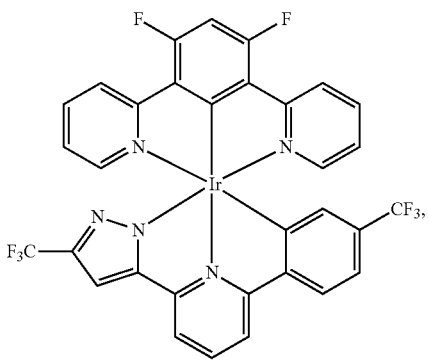

-continued

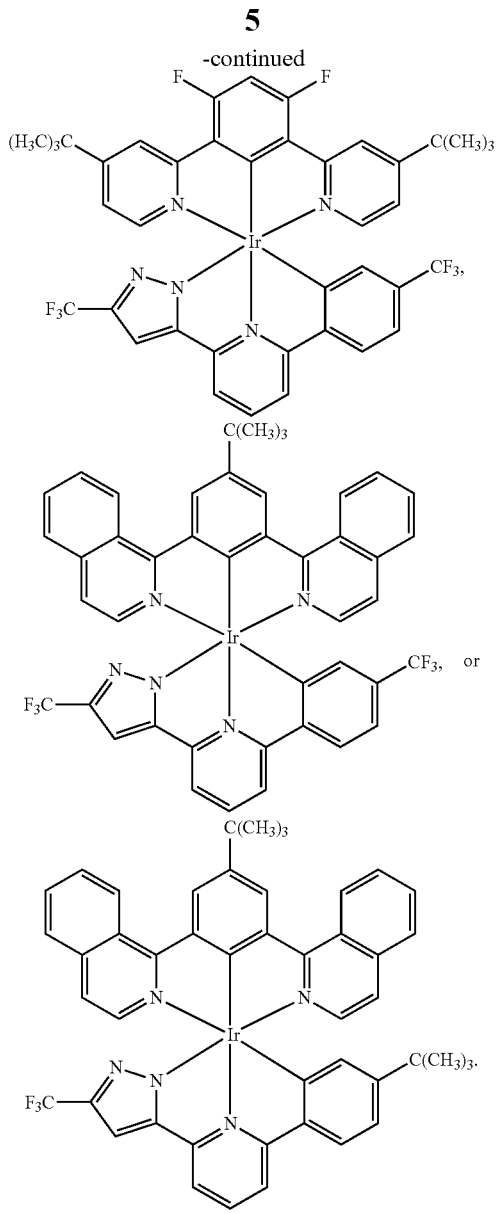

The bis-tridentate iridium complex may be synthesized by selecting suitable reactants and under suitable conditions. For example, the bis-tridentate iridium complex is synthesized by heating a first mixture including a pyridine-based compound and a chloride bridged dimer.

The pyridine-based compound is represented by a formula (II):

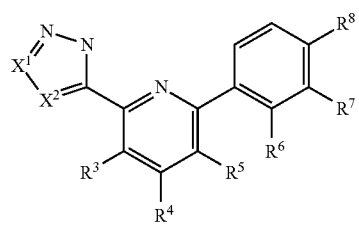

where $X^1$, $X^2$, $R^3$, $R^4$, $R^5$, $R^6$, $R^7$, and $R^8$ are as defined above.

The chloride bridged dimer is represented by a formula (III):

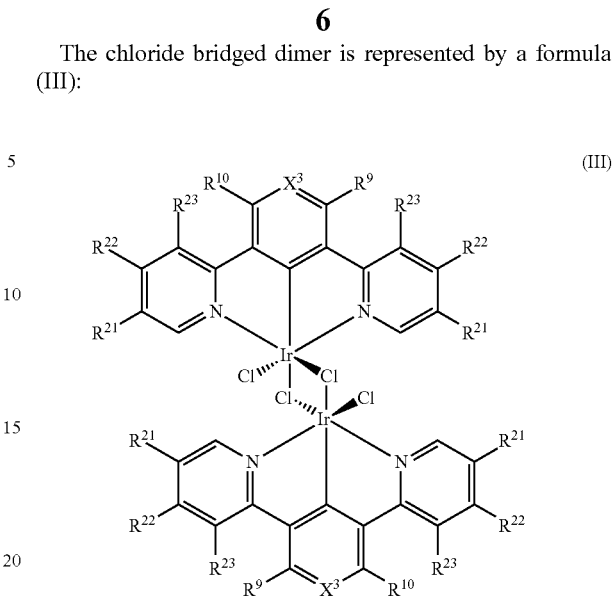

where $X^3$, $R^{21}$, $R^{22}$, $R^{23}$, $R^9$, and $R^{10}$ are as defined above. The chloride bridged dimer can be synthesized by heating a second mixture including an iridium source and a compound represented by a formula (IV):

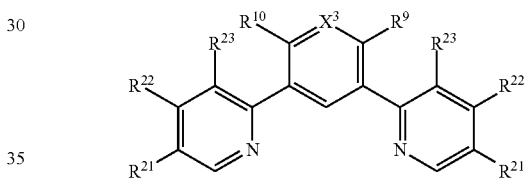

where $X^3$, $R^{21}$, $R^{22}$, $R^{23}$, $R^9$, and $R^{10}$ are as defined above.

Non-limiting examples of the iridium source include $IrCl_3 \cdot 3H_2O$, $[IrCl_3(tht)_3]$(tht=tetrahydrothiophene), $[Ir(COD)(\mu\text{-}Cl)]_2$ (COD=cyclooctadiene), etc.

The first mixture may further include a catalyst and various solvent. Non-limiting examples of the catalyst include sodium carbonate, sodium acetate, potassium acetate, sodium hydrogen carbonate, potassium carbonate, etc. Non-limiting examples of solvent include decalin (decahydronaphthalene), trimethylbenzene, xylene, dimethyl sulfoxide (DMSO), etc. Because the pyridine-based compound of the formula (II) has a five-membered heterocyclic ring, it has relatively high reactivity. Thus, it is feasible if a cheaper catalyst is selected to be used in the first reaction mixture.

The second mixture may further include another class of solvent. Non-limiting examples include 2-ethoxyethanol, 2-methoxyethanol, diethylene glycol monoethyl ether, diethylene glycol monomethyl ether, etc.

The bis-tridentate iridium complex can be excited by energy (such as light or electricity) to emit phosphorescence (visible light), and thus, may serve as a guest material of a light-emitting layer of an organic light-emitting diode (OLED). The bis-tridentate iridium complex with different tridentate ligands can be used to emit different colors of light.

The disclosure will now be explained in more detail below. It should be noted that the following compounds/complexes were synthesized for exemplification, not for limitation.

Synthesis of Compound L1

2-[3-(trifluoromethyl)-1H-pyrazol-5-yl]-6-[4-(trifluoromethyl)phenyl]-pyridine (Compound L1) was synthesized by the following steps.

(1-1) Synthesis of 1-(6-bromopyridin-2-yl)ethanone (Compound L1-1)

2,6-dibromopyridine (10.0 g, 42.2 mmol) was placed in a reaction flask. To ensure a nitrogen atmosphere in the reaction flask, the gas in the reaction flask was drawn out and the reaction flask was refilled with nitrogen gas in a rapid manner three times. To the reaction flask, 150 ml of anhydrous diethylether was added, and then 17.7 ml of an n-butyllithium solution (44.3 mmol, 2.5 M in n-hexane) was slowly added at −78° C. to obtain a mixture. In the meanwhile, the color of the mixture changed from transparent to yellowish-brown. The mixture in the reaction flask was kept at −78° C. and continuously stirred for 30 minutes. Then, N,N-dimethylacetamide (4.7 ml, 50.7 mmol) was slowly added to the mixture, and the mixture was kept at −78° C. for 3 hours for reaction. Thereafter, the temperature of the mixture was slowly raised to 20° C. At this moment, the color of the mixture in the reaction flask changed to cloudy gray. Deionized water was slowly added to the mixture to terminate the reaction in the reaction flask. The solvents in the mixture were drawn out of the reaction flask, and the residue in the reaction flask was washed several times with ethyl acetate and with a saturated sodium chloride solution to collect an organic layer, followed by dehydration of the organic layer using sodium sulfate ($Na_2SO_4$) to thereby obtain a crude product. The crude product was subjected to column chromatography ($SiO_2$, ethyl acetate:n-hexane=1:20), followed by recrystallization in a mixed solvent having dichloromethane and n-hexane (dichloromethane:n-hexane=1:20) at 20° C., thereby obtaining white crystals (6.80 g, 81% yield).

The spectrum analysis for the white crystals is: $^1$H NMR (400 MHz, $CDCl_3$): δ 7.97 (dd, J=7.0, 1.6 Hz, 1H), 7.68 (t, J=7.8 Hz, 1H), 7.64 (dd, J=8.0, 1.2 Hz, 1H), 2.69 (s, 3H). The white crystals were confirmed to be Compound L1-1 having a chemical structure represented by

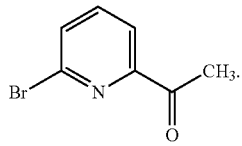

(1-2) Synthesis of 2-[4-(trifluoromethyl)phenyl]-4,4,5,5-tetramethyl-1,3,2-dioxaborolane (Compound L1-2)

4-bromobenzotrifluoride (4.8 g, 21.3 mmol) was placed in a reaction flask. To ensure a nitrogen atmosphere in the reaction flask, the gas in the reaction flask was drawn out and the reaction flask was refilled with nitrogen gas in a rapid manner three times. To the reaction flask, 50 ml of anhydrous diethylether was added, and then 10 ml of n-butyllithium solution (25.6 mmol, 2.5 M in n-hexane) was slowly added at −78° C. to obtain a mixture. In the meanwhile, the color of the mixture changed from transparent to cloudy green. The mixture was kept at −78° C. and continuously stirred for 60 minutes. Next, 2-isopropoxy-4,4,5,5-tetramethyl-1,3,2-dioxaborolane (5.2 ml, 25.6 mmol) was slowly added to the mixture at −78° C., and then the temperature was slowly raised to and kept at 20° C. for 12 hours for reaction. The color of the mixture in the reaction flask changed from cloudy green to cloudy white. Deionized water was slowly added to the mixture to terminate the reaction in the reaction flask. The solvents in the mixture were drawn out of the reaction flask, and the residue in the reaction flask was washed several times with ethyl acetate and with a saturated sodium chloride solution to collect an organic layer, followed by dehydration of the organic layer using sodium sulfate ($Na_2SO_4$) to thereby obtain a crude product. The crude product was recrystallized in a mixed solvent having dichloromethane and n-hexane (dichloromethane:n-hexane=1:1) at 20° C., thereby obtaining white crystals (4.27 g, 73% yield).

The spectrum analysis for the white crystals is: $^1$H NMR (400 MHz, CDCl3): δ 7.88 (d, J=8.0, 2H), 7.59 (d, J=8.0 Hz, 2H), 1.33 (s, 12H); $^{19}$F NMR (376 MHz, CDCl3, 298K): δ −63.06(s). The white crystals were confirmed to be Compound L1-2 having a chemical structure represented by

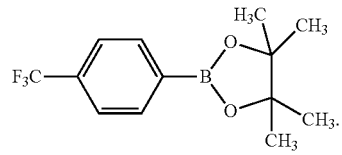

(1-3) Synthesis of 1-[6-(4-(trifluoromethyl)phenyl) pyridin-2-yl]ethanone (Compound L1-3)

Compound L1-1 (900 mg, 4.5 mmol), Compound L1-2 (1.36 g, 5 mmol), 11 ml of a sodium carbonate solution (2N, 22.5 mmol), and tetrakis(triphenylphosphine)palladium [Pd $(PPh_3)_4$] (260 mg, 0.22 mmol) were placed in a reaction flask, and then 27 ml of toluene and 3 ml of methanol were added to the reaction flask to obtain a mixture. The mixture was heated under reflux for 24 hours, and then the temperature of the mixture was slowly reduced to 20° C. The solvents in the mixture were drawn out of the reaction flask, and the residue in the reaction flask was washed several times with ethyl acetate and with a saturated sodium chloride solution to collect an organic layer, followed by dehydration of the organic layer using sodium sulfate ($Na_2SO_4$) to thereby obtain a crude product. The crude product was subjected to column chromatography ($SiO_2$, ethyl acetate:n-hexane=1:6), followed by recrystallization in a mixed solvent having dichloromethane and n-hexane (dichloromethane:n-hexane=1:1) at 20° C., thereby obtaining white crystals (891 mg, 75% yield).

The spectrum analysis for the white crystals is: $^1$H NMR (400 MHz, $CDCl_3$): δ 8.02 (d, J=6.4, 2H), 7.95 (d, J=7.6 Hz, 1H), 7.93~7.91 (m, 2H), 7.75 (d, J=8.0, 2H), 2.81 (s, 3H); $^{19}$F NMR (376 MHz, CDCl3, 298K): δ −62.59 (s, 3F). The white crystals were confirmed to be Compound L1-3 having a chemical structure represented by

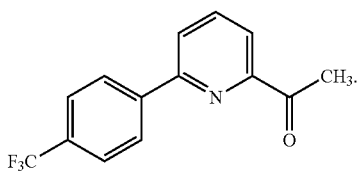

(1-4) Synthesis of Compound L1

In a reaction flask, sodium ethoxide (334.8 mg, 4.90 mmol) was dissolved in 50 ml of anhydrous tetrahydrofuran. The reaction flask was cooled in an ice bath, and the content therein was continuously stirred for 10 minutes. The reaction flask was maintained in the ice bath, and Compound L1-3 (870 mg, 3.28 mmol) was slowly added to and mixed with the content in the reaction flask by stirring for 1 hour. Then, ethyl trifluoroacetate (0.62 ml, 4.90 mmol) was added to the reaction flask to obtain a mixture, and the temperature was raised to 20° C. The mixture was heated under reflux for 12 hours for reaction. Next, the temperature was reduced to 20° C. The solvents in the mixture were drawn out of the reaction flask, and deionized water was added to the reaction flask to obtain a mixed solution. The pH of the mixed solution was adjusted to 5~6 using a hydrogen chloride solution (2N). Then, the mixed solution was washed several times with ethyl acetate to collect a first organic layer. The first organic layer was dehydrated using sodium sulfate ($Na_2SO_4$), and the solvent(s) in the first organic layer was removed to obtain an intermediate (1,3-dione derivative).

The intermediate was placed in a single neck flask, and was dissolved in 50 ml of ethanol. Then, hydrazine monohydrate (1.6 ml, 32.8 mmol) was added to the single-neck flask to obtain a sample solution. The sample solution was heated under reflux for 1 day. Thereafter, the solvents in the sample solution were removed, and the sample solution was washed several times with ethyl acetate and with a saturated sodium chloride solution to collect a second organic layer. The second organic layer was dehydrated using sodium sulfate ($Na_2SO_4$) to obtain a crude product. The crude product was subjected to column chromatography ($SiO_2$, ethyl acetate:n-hexane=1:3), followed by recrystallization in a mixed solvent having dichloromethane and n-hexane (dichloromethane:n-hexane=1:1) at 20° C., thereby obtaining white crystals (0.84 g, 70% yield).

The spectrum analysis for the white crystals is: $^1$H NMR (400 MHz, $CDCl_3$): δ 11.42 (br, 1H), 8.12 (d, J=8.0 Hz, 2H), 7.90 (t, J=7.8 Hz, 1H), 7.75 (d, J=8.0 Hz, 3H), 7.61 (d, J=8.0 Hz, 1H), 6.99 (s, 1H); $^{19}$F NMR (376 MHz, $CDCl_3$, 298 K): δ −62.35 (s, 3F), −62.69 (s, 3F). The white crystals were confirmed to be Compound L1 having a chemical structure represented by

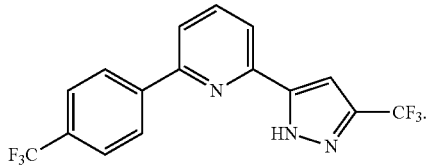 [SMILES: FC(F)(F)c1ccc(-c2cccc(-c3cc(C(F)(F)F)n[nH]3)n2)cc1]

Synthesis of Compound L2

2-[3-(tert-butyl)-1H-pyrazol-5-yl]-6-[4-(trifluoromethyl)phenyl]-pyridine (Compound L2) was synthesized by the following steps.

(2-1) Synthesis of 1-[6-(4-(tert-butyl)phenyl)pyridin-2-yl]ethanone (Compound L2-1)

Compound L2-1 was synthesized by procedures substantially the same as those in step 1-3 for synthesizing Compound L1-3, except that, in the synthesis of Compound L2-1 (step 2-1), 2-(4-tert-Butylphenyl)-4,4,5,5-tetramethyl-1,3,2-dioxaborolane (1.23 g, 4.74 mmol) was used to replace Compound L1-2 used in step 1-3, thereby obtaining a crude product. The crude product was subjected to column chromatography ($SiO_2$, ethyl acetate:n-hexane=1:5), followed by recrystallization in a mixed solvent having dichloromethane and n-hexane (dichloromethane:n-hexane=1:1) at 20° C., thereby obtaining light yellow crystals (1113 mg, 97.8% yield).

The spectrum analysis for the light yellow crystals is: $^1$H NMR (400 MHz, $CDCl_3$): δ 8.02 (d, $J_{HH}$=8.4 Hz, 2H), 7.94~7.83 (m, 3H), 7.52 (d, $J_{HH}$=8.4 Hz, 2H), 2.8 (s, 3H), 1.36 (s, 9H). The light yellow crystals were confirmed to be Compound L2-1 having a chemical structure represented by

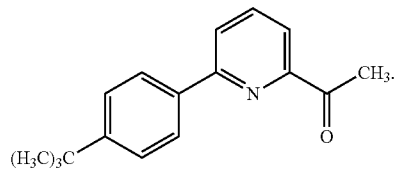 [SMILES: CC(=O)c1cccc(-c2ccc(C(C)(C)C)cc2)n1]

(2-2) Synthesis of Compound L2

Compound L2 was synthesized by procedures substantially the same as the procedures for synthesizing Compound L1 (step 1-4), except that, in the synthesis of Compound L2 (step 2-2), Compound L2-1 (253 mg, 1 mmol) was used to replace Compound L1-3 used in step 1-4, thereby obtaining a crude product. The crude product was subjected to column chromatography ($SiO_2$, ethyl acetate:n-hexane=1:5) to obtain white crystals (1877 mg, 56.1% yield).

The spectrum analysis for the white crystals is: $^1$H NMR (400 MHz, $CDCl_3$): δ 7.95 (dd, $J_{HH}$=8.4, 2.0 Hz, 2H), 7.83 (t, $J_{HH}$=8.0 Hz 1H), 7.70 (d, $J_{HH}$=8.0 Hz 1H), 7.54 (d, $J_{HH}$=2.0 Hz, 1H), 7.53~7.51 (m, 2H), 6.96 (s, 1H), 1.37 (s, 9H); $^{19}$F NMR (376 MHz, $CDCl_3$): δ −62.37 (s, 3F). The white crystals were confirmed to be Compound L2 having a chemical structure represented by

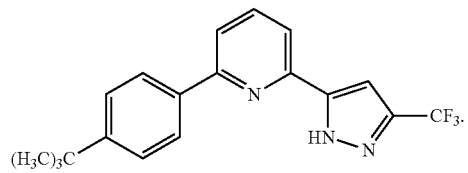 [SMILES: CC(C)(C)c1ccc(-c2cccc(-c3cc(C(F)(F)F)n[nH]3)n2)cc1]

Synthesis of Compound L3

1,3-di(2-pyridyl)-4,6-difluorobenzene (Compound L3) was synthesized by the following steps.

(3-1) Synthesis of 1,5-dibromo-2,4-difluorobenzene (Compound L3-1)

2,4-difluorobromobenzene (3 g, 15.5 mmol) and 260 mg of iron filings were placed in a two-neck flask, and 15 ml of dichloromethane was then added thereto. The two-neck flask was cooled in an ice bath, and a solution including bromine (1 ml, 18.7 mmol) and 15 ml of dichloromethane was added dropwise to the two-neck flask using an isobaric funnel. Next, the contents in the two-neck flask were heated under reflux for 3 hours. During heating, brown gas was produced. Then, the temperature was reduced to 20° C., and 50 ml of a sodium metabisulfite ($Na_2S_2O_5$) aqueous solution (10%) was mixed with the contents in the two-neck flask by stirring for 1 hour for terminating the reaction therein. Thereafter, the contents in the two-neck flask were washed several times with deionized water to collect an organic layer, the organic layer was dehydrated using sodium sulfate ($Na_2SO_4$), and the solvent in the organic layer was removed, followed by column chromatography ($SiO_2$, n-hexane), thereby obtaining white crystals (3.5 g, 83% yield).

The spectrum analysis for the white crystals is: $^1$H NMR (400 MHz, $CDCl_3$): δ 7.74 (t, J=7.6 Hz, 1H), 6.96 (t, J=8.0 Hz, 1H); $^{19}$F NMR (376 MHz, $CDCl_3$, 298 K): δ −103.8 (dd, J=7.5 Hz, J=7.5 Hz). The white crystals were confirmed to be Compound L3-1 having a chemical structure represented by

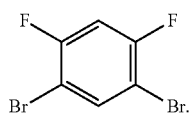

(3-2) Synthesis of 2-(tributylstannyl)pyridine (Compound L3-2)

2-bromopyridine (3.3 g, 21.0 mmol) was placed in a reaction flask. To ensure a nitrogen atmosphere in the reaction flask, the gas in the reaction flask was drawn out and the reaction flask was refilled with nitrogen gas in a rapid manner three times. To the reaction flask, 30 ml of anhydrous tetrahydrofuran was added, and then 9 ml of an n-butyllithium solution (23.0 mmol, 2.5 M in n-hexane) was slowly added at −78° C. to obtain a mixture. The mixture was kept at −78° C. and stirred for 60 minutes. At this moment, the color of the mixture changed from clear dark brown to cloudy yellowish green. Next, tributyltin chloride (6.3 ml, 23.0 mmol) was slowly added to the mixture at −78° C. for reaction for 3 hours. Thereafter, the temperature of the mixture was raised to 20° C., and the mixture was continuously stirred for 30 minutes to allow the color of the mixture to change to clear yellow. Then, a saturated ammonium chloride ($NH_4Cl$) aqueous solution was slowly added to the mixture to terminate the reaction. The solvents in the mixture were drawn out of the reaction flask, and the residue in the reaction flask was washed several times with ethyl acetate and with a saturated sodium chloride aqueous solution to collect an organic layer. The organic layer was dehydrated using sodium sulfate ($Na_2SO_4$) to obtain a dark brown liquid (7.53 g, 98% yield).

The spectrum analysis for the dark brown liquid is: $^1$H NMR (400 MHz, $CDCl_3$): δ 8.66 (d, J=1.2 Hz, 1H), 7.49 (m, 1H), 7.40 (d, J=1.2 Hz, 1H), 7.09~7.13 (m, 1H), 1.57 (m, 6H), 1.30~1.35 (m, 6H), 1.10~1.14 (m, 6H), 0.88 (t, J=7.2 Hz, 9H). The dark brown liquid was confirmed to be Compound L3-2 having a chemical structure represented by

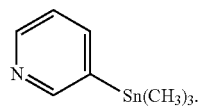

(3-3) Synthesis of Compound L3

Bis(triphenylphosphine)palladium(II) dichloride [Pd$(PPh_3)_2Cl_2$] (0.12 g, 0.17 mmol) and Compound L3-1 (1.5 g, 5.5 mmol) were placed in a reaction flask. Then, lithium chloride (1.4 g, 33.1 mmol), Compound L3-2 (6 g, 16.6 mmol), and 40 ml of anhydrous toluene were added to the reaction flask to obtain a mixture. The mixture was heated under reflux for 3 days. Next, the temperature of the mixture was slowly reduced to 20° C., and the mixture was filtered using celite to remove side products and to collect a filtrate. The solvents in the filtrate was removed, and then the filtrate was washed several times with ethyl acetate and with a saturated sodium chloride aqueous solution to collect an organic layer. The organic layer was dehydrated using sodium sulfate ($Na_2SO_4$) to obtain a crude product. The crude product was subjected to column chromatography ($SiO_2$, ethyl acetate:n-hexane=1:3), followed by recrystallization in a mixed solvent having dichloromethane and n-hexane (dichloromethane:n-hexane=1:1) at 20° C., thereby obtaining transparent crystals (780 mg, 53% yield).

The spectrum analysis for the transparent crystals is: $^1$H NMR (400 MHz, $d_6$-acetone): δ 8.84 (t, J=6.8 Hz, 1H), 8.74 (d, J=4.8 Hz, 2H), 7.94~7.87 (m, 4H), 7.41~7.38 (m, 2H), 7.29 (t, J=9.4 Hz, 1H); $^{19}$F NMR (376 MHz, $d_6$-acetone, decouple H, 298 K): δ −112.95. The transparent crystals were confirmed to be Compound L3 having a chemical structure represented by

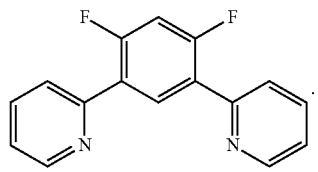 [SMILES: Fc1cc(F)c(-c2ccccn2)cc1-c1ccccn1]

Synthesis of Compound L4

2,2'-(4,6-difluoro-1,3-phenylene)bis[4-(tert-butyl)pyridine](Compound L4) was synthesized by the following steps.

(4-1) Synthesis of 4-(tert-butyl)pyridine N-oxide (Compound L4-1)

In a reaction flask, 4-(tert-butyl)pyridine (13.5 g, 99.8 mmol) was dissolved in 70 ml of acetic acid (1.29 mmol), and 30 ml of hydrogen peroxide ($H_2O_2$) (30%, 0.30 mol) was then slowly added to obtain a mixture. The mixture was heated to 80° C. for reaction for 24 hours, and the temperature was then slowly reduced to 20° C. The reaction flask was vacuum pumped to remove solvents from the mixture, followed by addition of a sodium hydroxide aqueous solution to adjust the pH of the mixture to 8. Next, the mixture was washed several times with dichloromethane and with deionized water to collect an organic layer, and the organic layer was dehydrated using sodium sulfate ($Na_2SO_4$). The solvent was then removed from the organic layer, followed by vacuum drying, thereby obtaining light yellow solids (13 g, 87% yield), which was Compound L4-1 having a chemical structure represented by

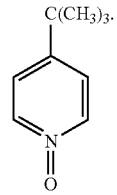

(4-2) Synthesis of 4-(tert-butyl)-2-chloropyridine (Compound L4-2)

Compound L4-1 (5 g, 33.07 mmol) was placed in a two-neck flask. The two-neck flask was cooled in an ice bath, and 25 ml of phosphoryl chloride ($POCl_3$) was slowly added to the two-neck flask to obtain a mixture. The mixture was heated under reflux for 24 hours for reaction. Thereafter, the temperature was slowly reduced to 20° C., the solvent was removed from the mixture by vacuum pumping, a sodium carbonate aqueous solution was added to the two-neck flask for neutralization, and the contents in the two-neck flask were extracted using ethyl acetate to collect an organic layer. The organic layer was dehydrated using sodium sulfate ($Na_2SO_4$) to obtain a crude product. The crude product was subjected to column chromatography ($SiO_2$, ethyl acetate:n-hexane=1:6), thereby obtaining a transparent liquid (4 g, 72% yield).

The spectrum analysis for the transparent liquid is: $^1$H-NMR (400 MHz, $CDCl_3$): δ 8.27 (d, J=5.3 Hz, 1H), 7.28 (s, 1H), 7.19 (dd, J=5.2 Hz, 1.6 Hz, 1H), 1.29 (s, 9H). The transparent liquid was confirmed to be Compound L4-2 having a chemical structure represented by

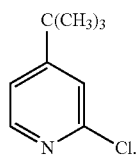 [SMILES: CC(C)(C)c1ccnc(Cl)c1]

(4-3) Synthesis of 4-(tert-butyl)-2-bromopyridine (Compound L4-3)

Compound L4-2 (3 g, 17.6 mmol) and trimethylsilyl bromide (7 ml, 53.05 mmol) were placed in a reaction flask, and 50 ml of propionitrile was then added to the reaction flask to obtain a mixture. The mixture was heated under reflux for reaction for 24 hours, and was allowed to cool to 20° C., followed by further addition of trimethylsilyl bromide (7 ml, 53.05 mmol) to the reaction flask. Next, the contents in the reaction flask were further heated under reflux for another 24 hours, and then the temperature was slowly reduced to 20° C. Thereafter, the reaction flask was vacuum pumped to remove the solvents from the contents in the reaction flask, a sodium carbonate aqueous solution was added to the reaction flask for neutralization, and the contents in the reaction flask were extracted using ethyl acetate to collect a first organic layer. The first organic layer was dehydrated using sodium sulfate ($Na_2SO_4$), and was washed several times with ethyl acetate and with a saturated sodium chloride aqueous solution to collect a second organic layer. The second organic layer was dehydrated using sodium sulfate ($Na_2SO_4$) to obtain a crude product. The crude product was subjected to column chromatography ($SiO_2$, ethyl acetate:n-hexane=1:6), thereby obtaining a yellow oil (3 g, 80% yield).

The spectrum analysis for the yellow oil is: $^1$H NMR (400 MHz, $CDCl_3$): δ 8.22 (d, J=5.2 Hz, 1H), 7.41 (s, 1H), 7.20 (dd, J=5.2 Hz, 1.6 Hz, 1H), 1.26 (s, 9H). The yellow oil was confirmed to be Compound L4-3 having a chemical structure represented by

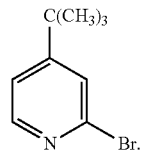

(4-4) Synthesis of 2,2'-(4,6-difluoro-1,3-phenylene) bis(4,4,5,5-tetramethyl-1,3,2-dioxaborolane) (Compound L4-4)

1,3-dibromo-4,6-difluorobenzene (300 mg, 1.1 mmol), bis (pinacolato)diboron (620 mg, 2.4 mmol), [1,1'-bis(diphenylphosphino)ferrocene]dichloropallad ium(II) [Pd(dppf)$Cl_2$](54 mg, 0.07 mmol), and potassium acetate (545 mg, 5.6 mmol) were placed in a reaction flask. To ensure a nitrogen atmosphere in the reaction flask, the gas in the reaction flask was drawn out by vacuum pumping and the reaction flask was refilled with nitrogen gas three times. To the reaction flask, 5 ml of dimethyl sulfoxide (DMSO) was added to obtain a mixture. The mixture was heated to and kept at 85° C. for reaction for 18 hours. Thereafter, the temperature of the mixture was slowly reduced to 20° C., the solvents in the mixture were removed from the reaction flask by vacuum pumping, and the residue in the reaction flask was washed several times with ethyl acetate and with a saturated sodium chloride aqueous solution to collect an organic layer. The organic layer was dehydrated using sodium sulfate ($Na_2SO_4$) to obtain a crude product. The crude product was subjected to column chromatography ($SiO_2$, ethyl acetate:n-hexane=1:4), and then was dissolved in n-hexane at a relatively high temperature, followed by cooling in a refrigerator for 12 hours, thereby obtaining white solids (496 mg, 45% yield).

The spectrum analysis for the white solids is: 1H NMR (400 MHz, $CDCl_3$): δ 8.11 (t, J=7.5 Hz, 1H), 6.71 (t, J=9.2 Hz, 1H), 1.33 (s, 24H); $^{19}$F NMR (376 MHz, $CDCl_3$, 298 K): δ −94.18 (t, J=11.2 Hz). The white solids were confirmed to be Compound L4-4 having a chemical structure represented by

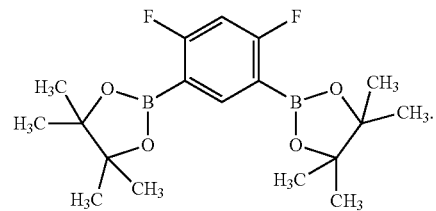

(4-5) Synthesis of Compound L4

Bis(triphenylphosphine)palladium(II) dichloride [Pd($PPh_3$)$_2Cl_2$](0.32 g, 0.27 mmol), Compound L4-4 (1 g, 2.7 mmol), Compound L4-3 (1.29 g, 6 mmol), and 15 ml of a sodium carbonate solution (2N) were placed in a reaction flask, and 15 ml of dimethoxyethane was then added thereto to obtain a mixture. The mixture was heated under reflux for reaction for 2 days, and the temperature was slowly reduced to 20° C. The solvents in the mixture were removed from the reaction flask, and the residue in the reaction flask was washed several times with ethyl acetate and with a saturated sodium chloride aqueous solution to collect an organic layer.

The organic layer was dehydrated using sodium sulfate ($Na_2SO_4$) to obtain a crude product. The crude product was subjected to column chromatography ($SiO_2$, ethyl acetate:n-hexane=1:3.5), thereby obtaining a colorless liquid (520 mg, 50% yield).

The spectrum analysis for the colorless liquid is: $^1$H NMR (400 MHz, $d_6$-acetone): δ 8.74 (t, J=9.2 Hz, 1H), 8.64 (d, J=5.2 Hz, 2H), 7.88 (s, 2H), 7.43 (dd, J=5.2, 2.0 Hz, 2H), 7.30 (t, J=11.2 Hz, 1H), 1.38 (s, 18H); $^{19}$F NMR (376 MHz, $d_6$-acetone, 298 K): δ −113.42 (t, J=10.2 Hz). The colorless liquid was confirmed to be Compound L4 having a chemical structure represented by

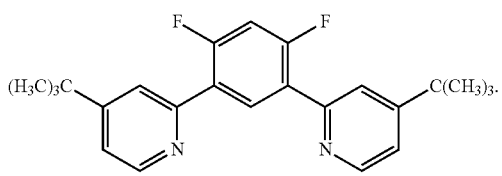 [SMILES: CC(C)(C)c1ccnc(-c2cc(-c3cc(C(C)(C)C)ccn3)c(F)cc2F)c1]

Synthesis of Compound L5

2,2'-[5-(tert-butyl)-1,3-phenylene]dipyridine (Compound L5) was synthesized by the following steps.

(5-1) Synthesis of 2,2'-[5-(tert-butyl)-1,3-phenylene]bis(4,4,5,5-tetramethyl-1,3,2-dioxaborolane) (Compound L5-1)

1,3-dibromo-5-tert-butylbenzene (2.9 g, 10 mmol), bis(pinacolato)diboron (5 g, 20 mmol), potassium acetate (4.9 g, 50 mmol), [1,1'-bis(diphenylphosphino)ferrocene]dichloropalladium(II) (0.5 g, 0.7 mmol), and 100 ml of 1,4-dioxane were placed in a reaction flask to obtain a mixture. The mixture was reacted at 100° C. under nitrogen atmosphere for 12 hours, and was then cooled. The mixture was mixed with water and extracted using ethyl acetate to collect an organic layer. The organic layer was washed with a saturated sodium chloride aqueous solution, and dried using anhydrous sodium sulfate ($Na_2SO_4$), followed by removal of solvents under a reduced pressure to obtain a crude product. The crude product was subjected to column chromatography ($SiO_2$, n-hexane) to give white solids (2.4 g, 63% yield).

The spectrum analysis for the white solids is: $^1$H NMR (CDCl$_3$, 400 MHz): δ 8.09 (s, 1H), 7.91 (s, 2H), 1.34 (s, 9H), 1.32 (s, 24H). The white solids were confirmed to be Compound L5-1 having a chemical structure represented by

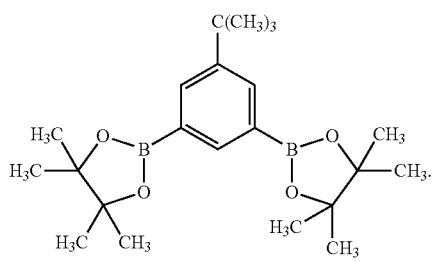 [SMILES: CC(C)(C)c1cc(B2OC(C)(C)C(C)(C)O2)cc(B2OC(C)(C)C(C)(C)O2)c1]

(5-2) Synthesis of Compound L5

2-Bromopyridine (3.2 g, 20 mmol), Compound L5-1 (3.9 g, 10 mmol), sodium carbonate (3 g, 30 mmol), tetrakis (triphenylphosphine)palladium [Pd(PPh$_3$)$_4$] (0.5 g, 0.4 mmol), 15 ml of dimethoxyethane, and 15 ml of deionized water were placed in a reaction flask to obtain a mixture. The mixture was reacted at 100° C. under nitrogen atmosphere for 24 hours, and was then cooled. Thereafter, the mixture was mixed with deionized water and extracted using ethyl acetate to collect an organic layer. The organic layer was washed with a saturated sodium chloride solution and dehydrated using sodium sulfate ($Na_2SO_4$), followed by removal of solvent under a reduced pressure to obtain a crude product. The crude product was subjected to column chromatography ($SiO_2$, n-hexane: ethyl acetate=1:5), thereby obtaining white solids (2.4 g, 63% yield).

The spectrum analysis for the white solids is: $^1$H NMR (CDCl$_3$, 400 MHz): δ 8.70 (d, J=5.6 Hz, 2H), 8.35 (s, 1H), 8.12 (s, 2H), 7.81 (d, J=6.0 Hz, 2H), 7.73 (t, J=7.6 Hz, 2H), 7.19~7.22 (m, 2H), 1.44 (s, 9H). The white solids were confirmed to be Compound L5 having a chemical structure represented by

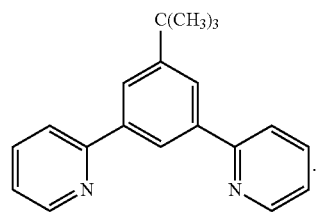 [SMILES: CC(C)(C)c1cc(-c2ccccn2)cc(-c2ccccn2)c1]

Synthesis of Compound L6

1,1'-[5-(tert-butyl)-1,3-phenylene]diisoquinoline (Compound L6) was synthesized by step 6 similar to step 5-2 for synthesizing Compound L5, except that, in step 6, 1-chloroisoquinoline (3.3 g, 20 mmol) was used to replace 2-bromopyridine used in step 5-2, to thereby obtain a crude product. The crude product was subjected to column chromatography ($SiO_2$, ethyl acetate:n-hexane=1:4), thereby obtaining white solids (4 g, 52% yield).

The spectrum analysis for the white solids is: $^1$H NMR (CDCl$_3$, 400 MHz): δ 8.60 (d, J=6.0 Hz, 2H), 8.16 (d, J=9.2 Hz, 2H), 7.85 (s, 2H), 7.82 (d, J=8.0 Hz, 2H), 7.79 (t, J=1.6 Hz, 1H), 7.60~7.64 (m, 4H), 7.49 (t, J=7.2 Hz, 2H), 1.42 (s, 9H). The white solids were confirmed to be Compound L6 having a chemical structure represented by

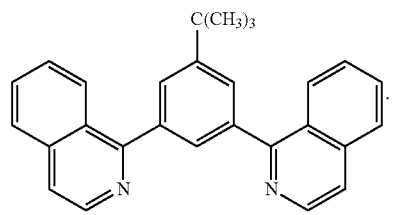 [SMILES: CC(C)(C)c1cc(-c2nccc3ccccc23)cc(-c2nccc3ccccc23)c1]

Synthesis of Dimer 1

IrCl$_3$.3H$_2$O (200 mg, 0.57 mmol) and Compound L3 (153 mg, 0.57 mmol) were placed in a reaction flask, and then 14 ml of 2-ethoxyethanol and 6 ml of deionized water was added to the reaction flask to obtain a mixture. The mixture was heated under reflux for reaction. At the meantime, the color of the mixture changed from cloudy black to cloudy yellow. After reaction for 24 hours, the mixture was allowed to cool to 20° C., and was filtered to collect a solid fraction. The solid fraction was sequentially washed with diethyl ether and ethanol, and was then dried to obtain yellow solids (236 mg, 77% yield).

The spectrum analysis for the yellow solids is: $^1$H NMR (400 MHz, d$_6$-DMSO): δ 9.07 (d, J=5.6 Hz, 4H), 8.14 (d, J=3.7 Hz, 8H), 7.65~7.61 (m, 4H), 7.25 (t, J=11.6 Hz, 2H); $^{19}$F NMR (376 MHz, d$_6$-DMSO, 298 K): δ −106.94 (t, J=12.1 Hz). The yellow solids were confirmed to be a chloride bridged dimer (Dimer 1) having a chemical structure represented by

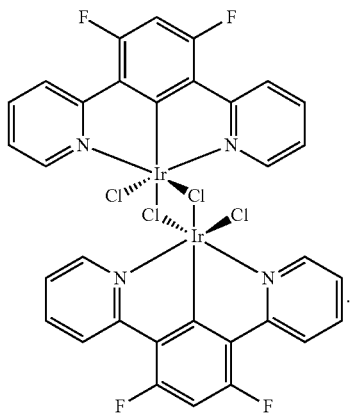

Synthesis of Dimer 2

Dimer 2 was synthesized according to the procedures for synthesizing Dimer 1, except that, in the synthesis of Dimer 2, Compound L4 (217 mg, 0.57 mmol) was used to replace Compound L3 used for synthesizing Dimer 1. A solid fraction obtained in the procedures for synthesizing Dimer 2 was sequentially washed with diethyl ether and ethanol, and was then dried to obtain yellow solids (275 mg, 75% yield).

The spectrum analysis for the yellow solids is: $^1$H NMR (400 MHz, d$_6$-DMSO): δ 8.91 (d, J=6.2 Hz, 4H), 8.03 (s, 4H), 7.70 (d, J=6.2 Hz, 4H), 7.24 (t, J=10.5 Hz, 2H), 1.38 (s, 36H); $^{19}$F NMR (376 MHz, d$_6$-DMSO, 298 K): δ −107.51 (t, J=11.9 Hz). The yellow solids were confirmed to be a chloride bridged dimer (Dimer 2) having a chemical structure represented by

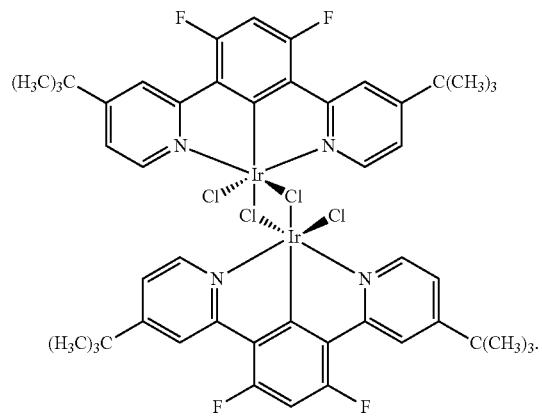

Synthesis of Dimer 3

Dimer 3 was synthesized according to the procedures for synthesizing Dimer 1, except that, in the synthesis of Dimer 3, Compound L5 (164 mg, 0.57 mmol) was used to replace Compound L3 used for synthesizing Dimer 1. A solid fraction obtained in the procedures for synthesizing Dimer 3 was sequentially washed with diethyl ether and ethanol, and was then dried to obtain brown yellow solids (227 mg, 72.5% yield).

The spectrum analysis for the brown yellow solids is: $^1$H NMR (400 MHz, d$_6$-DMSO): δ 9.01 (d, J=4.8 Hz, 4H), 8.32 (t, J=7.2 Hz, 4H), 7.99 (s, 4H), 7.92 (t, J=7.6 Hz, 4H), 7.35 (t, J=7.2 Hz, 4H), 1.44 (s, 18H). The brown yellow solids were confirmed to be a chloride bridged dimer (Dimer 3) having a chemical structure represented by

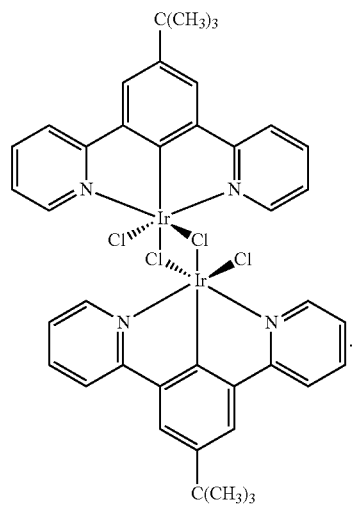

Synthesis of Dimer 4

Dimer 4 was synthesized according to the procedures for synthesizing Dimer 1, except that, in the synthesis of Dimer 4, Compound L6 (221 mg, 0.57 mmol) was used to replace Compound L3 used for synthesizing Dimer 1. A solid fraction obtained in the procedures for synthesizing Dimer 4 was sequentially washed with diethyl ether and ethanol, and was then dried to obtain red solids (286 mg, 77% yield).

The spectrum analysis for the red solids is: $^1$H NMR (400 MHz, d$_6$-DMSO): δ 9.17 (d, J=6.4 Hz, 2H), 9.09 (t, J=7.6 Hz, 4H), 8.93 (s, 2H), 8.56 (d, J=6.4 Hz, 4H), 8.22 (d, J=8.0 Hz, 4H), 8.05 (d, J=6.4 Hz, 2H), 7.96~8.02 (m, 6H), 7.87~7.94 (m, 4H), 1.58 (s, 9H), 1.57 (s, 9H). The red solids were confirmed to be a chloride bridged dimer (Dimer 4) having a chemical structure represented by

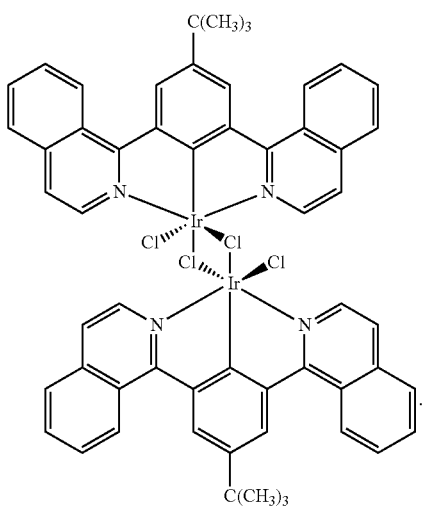

Example 1

EX 1

Synthesis of bis-tridentate iridium complex 1

(Complex 1)

Dimer 1 (50 mg, 0.046 mmol) and Compound L1 (42 mg, 0.11 mmol) were placed in a reaction flask, and sodium acetate (82 mg, 1.0 mmol) and 20 ml of decalin were added to the reaction flask to obtain a mixture. The mixture was heated under reflux and under nitrogen atmosphere for reaction for 24 hours, and was then allowed to cool to room temperature, followed by removal of the solvent using vacuum pumping, thereby obtaining a crude product. The crude product was subjected to column chromatography ($SiO_2$, dichloromethane:ethyl acetate=5:1), followed by recrystallization in a mixed solvent having dichloromethane and n-hexane (dichloromethane:n-hexane=1:1), thereby obtaining bright yellow crystals (54 mg, 72% yield).

The spectrum analysis for the bright yellow crystals is: $^1$H NMR (400 MHz, $CDCl_3$): δ 8.10 (d, J=4.0 Hz, 2H), 7.96 (t, J=8.0 Hz, 1H), 7.81 (d, J=8.0 Hz, 1H), 7.76 (d, J=8.0 Hz, 1H), 7.62~7.55 (m, 4H), 7.30 (d, J=4.0 Hz, 2H), 6.99 (d, J=8.0 Hz, 1H), 6.88 (s, 1H), 6.73 (t, J=4.0 Hz, 2H), 6.06 (s, 1H); $^{19}$F NMR (376 MHz, $CDCl_3$, 298 K): δ −60.15 (s, 3F), −62.85 (s, 3F), −107.65 (d, J=12.4 Hz, 2F); MS[FAB], m/z 816.1, M$^+$; $C_{32}H_{16}F_8IrN_5 \cdot H_2O$ elemental analysis (calculated): C, 44.24; H, 2.55; N, 8.06%; theory: C, 44.55; H, 2.58; N, 7.99%. The bright yellow crystals were confirmed to be Complex 1 having a chemical structure represented by

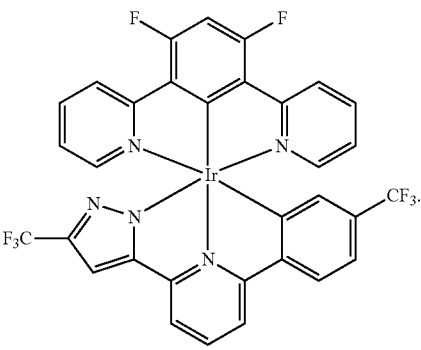

Example 2

EX 2

Synthesis of bis-tridentate iridium complex 2

(Complex 2)

Complex 2 of Example 2 was synthesized according to the procedures used in Example 1, except that, in Example 2, Dimer 2 (59 mg, 0.046 mmol) was used to replace Dimer 1 used in Example 1. A crude product obtained in the procedures for synthesizing Complex 2 was subjected to column chromatography ($SiO_2$, dichloromethane:ethyl acetate=5:1), followed by recrystallization in a mixed solvent having dichloromethane and n-hexane (dichloromethane:n-hexane=1:1), thereby obtaining bright yellow crystals (48 mg, 56% yield).

The spectrum analysis for the bright yellow crystals is: $^1$H NMR (400 MHz, $CDCl_3$): δ 8.09 (s, 2H), 7.93 (d, J=8.0 Hz, 1H), 7.79 (d, J=8.0 Hz, 1H), 7.74 (d, J=8.0 Hz, 1H), 7.61 (d, J=8.0 Hz, 1H), 7.15 (d, J=8.0 Hz, 2H), 7.00 (d, J=8.0 Hz, 1H), 6.89 (s, 1H), 6.83 (t, J=8.0 Hz, 1H), 6.72~6.70 (m, 2H), 6.12 (s, 1H), 1.24 (s, 18H); $^{19}$F NMR (376 MHz, $CDCl_3$, 298 K): δ −59.98 (s, 3F), −62.68 (s, 3F), −108.43 (d, J=4.0 Hz, 2F); MS[FAB], m/z 926, M$^+$; $C_{40}H_{32}F_8IrN_5$ elemental analysis (calculated): C, 51.83; H, 3.48; N, 7.56%; theory: C, 51.51; H, 3.51; N, 7.63%. The bright yellow crystals were confirmed to be Complex 2 having a chemical structure represented by

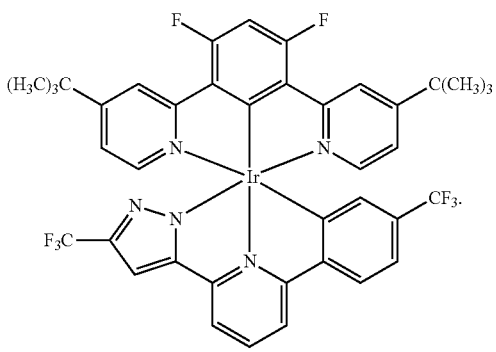

Example 3

EX 3

Synthesis of bis-tridentate iridium complex 3

(Complex 3)

Complex 3 of Example 3 was synthesized according to the procedures used in Example 1, except that, in Example 3, Dimer 3 (51 mg, 0.046 mmol) was used to replace Dimer 1 used in Example 1. A crude product obtained in the procedures for synthesizing Complex 3 was subjected to column chromatography ($Al_2O_3$, dichloromethane:n-hexane=1:1), followed by recrystallization in a mixed solvent having dichloromethane and n-hexane (dichloromethane:n-hexane=1:1), thereby obtaining bright yellow crystals (52 mg, 68% yield).

The spectrum analysis for the bright yellow crystals is: $^1$H NMR ($CDCl_3$, 400 MHz): δ 8.10 (s, 2H), 7.97~8.01 (m, 3H), 7.90 (d, J=8.0 Hz, 1H), 7.82 (d, J=8.0 Hz, 1H), 7.70 (d, J=8.4 Hz, 1H), 7.63 (t, J=8.4 Hz, 2H), 7.40 (d, J=5.6 Hz, 2H), 7.0 (d, J=10.0 Hz, 1H), 6.91 (s, 1H), 6.77 (t, J=7.2 Hz, 2H) 6.07 (s, 1H), 1.62 (s, 9H); $^{19}$F NMR ($CDCl_3$, 376 MHz): δ −60.67 (s, 3F), −63.16 (s, 3F); MS[FAB], m/z 836.1, [M+H]$^+$. The bright yellow crystals were confirmed to be Complex 3 having a chemical structure represented by

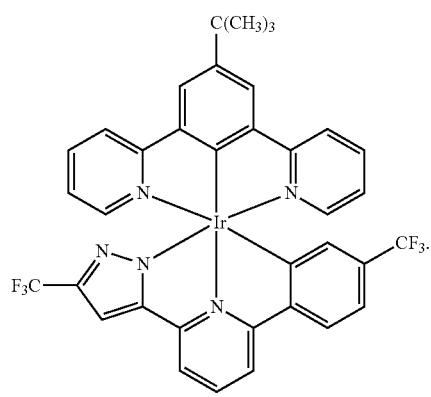

Example 4

EX 4

Synthesis of bis-tridentate iridium complex 4

(Complex 4)

Complex 4 of Example 4 was synthesized according to the procedures used in Example 1, except that, in Example 4, Dimer 4 (60 mg, 0.046 mmol) was used to replace Dimer 1 used in Example 1. A crude product obtained in the procedures for synthesizing Complex 4 was subjected to column chromatography ($Al_2O_3$, dichloromethane:n-hexane=1:1), followed by recrystallization in a mixed solvent having dichloromethane and n-hexane (dichloromethane:n-hexane=1:1), thereby obtaining red crystals (45 mg, 52% yield).

The spectrum analysis for the red crystals is: $^1$H NMR ($CDCl_3$, 400 MHz): δ 9.23 (d, J=8.8 Hz, 2H), 8.91 (s, 2H), 8.06 (t, J=8.0 Hz, 1H), 7.94 (d, J=8.0 Hz, 1H), 7.90 (d, J=8.0 Hz, 1H), 7.84 (t, J=8.4 Hz, 2H), 7.80 (d, J=68 Hz, 2H), 7.74 (d, J=6.8 Hz, 1H), 7.73 (t, J=7.6 Hz, 1H), 7.68 (d, J=8.0 Hz, 1H), 7.36 (d, J=6.4 Hz, 2H), 7.15 (d, J=6.4 Hz, 2H), 6.93 (d, J=7.6 Hz, 2H), 5.63 (s, 1H), 1.73 (s, 9H); $^{19}$F NMR ($CDCl_3$, 376 MHz): δ −60.73 (s, 3F), −63.34 (s, 3F); MS [FAB], m/z 936, [M+H]$^+$. The red crystals were confirmed to be Complex 4 having a chemical structure represented by

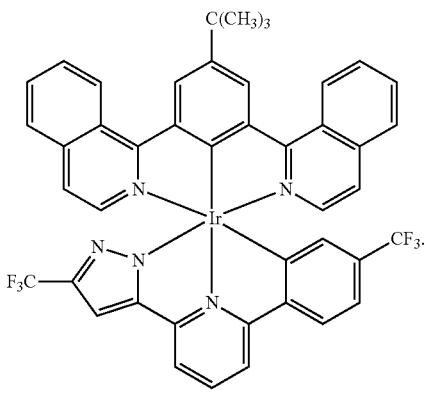

Example 5

EX 5

Synthesis of bis-tridentate iridium complex 5

(Complex 5)

Complex 5 of Example 5 was synthesized according to the procedures used in Example 1, except that, in Example 5, Dimer 3 (55 mg, 0.05 mmol) and Compound L2 (35 mg, 0.1 mmol) were used to replace Dimer 1 and Compound L1 used in Example 1, respectively. A crude product obtained in the procedures for synthesizing Complex 5 was subjected to column chromatography ($Al_2O_3$, dichloromethane), followed by recrystallization in a mixed solvent having dichloromethane and n-hexane (dichloromethane:n-hexane=1:1), thereby obtaining bright yellow crystals (46 mg, 56% yield).

The spectrum analysis for the bright yellow crystals is: $^1$H NMR (400 MHz, $CDCl_3$): δ 7.92 (d, J=7.6 Hz, 2H), 7.87 (d, J=8.4 Hz, 2H), 7.78 (d, J=8.0 Hz, 1H), 7.74 (d, J=7.6 Hz, 1H), 7.54 (t, J=8.4 Hz, 2H), 7.44 (d, J=8.4 Hz, 1H), 7.41 (t, J=7.6 Hz, 1H), 7.34 (d, J=5.6 Hz, 2H), 6.95 (s, 1H), 6.77 (d, J=8.4 Hz, 1H), 6.70 (t, J=5.6 Hz, 2H), 5.70 (s, 1H), 1.24 (s, 9H), 0.85 (s, 9H); $^{19}$F NMR (376 MHz, $CDCl_3$): δ −59.88 (s, 3F); MS[FAB], m/z 824, [M+H]$^+$. The bright yellow crystals were confirmed to be Complex 5 having a chemical structure represented by

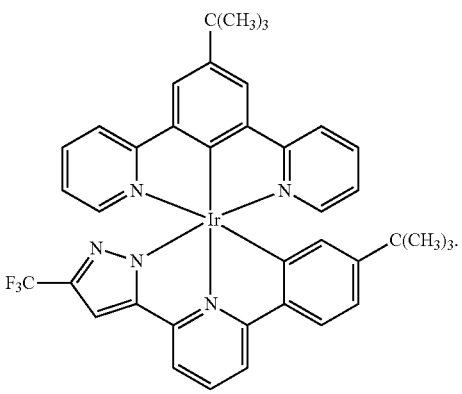

Example 6

EX 6

Synthesis of bis-tridentate iridium complex 6

(Complex 6)

Complex 6 of Example 6 was synthesized according to the procedures used in Example 1, except that, in Example 6, Dimer 4 (65 mg, 0.05 mmol) and Compound L2 (35 mg, 0.1 mmol) were used to replace Dimer 1 and Compound L1 used in Example 1, respectively. A crude product obtained in the procedures for synthesizing Complex 6 was subjected to column chromatography ($Al_2O_3$, dichloromethane), followed by recrystallization in a mixed solvent having dichloromethane and n-hexane (dichloromethane:n-hexane=1:1), thereby obtaining red crystals (58 mg, 63% yield).

The spectrum analysis for the red crystals is: $^1$H NMR (400 MHz, $CDCl_3$): δ 9.13 (d, J=8.8 Hz, 2H), 8.79 (s, 2H), 7.91 (t, J=7.6 Hz, 1H), 7.73~7.77 (m, 4H), 7.71 (d, J=7.2 Hz, 2H), 7.64 (t, J=7.6 Hz, 2H), 7.42 (d, J=8.0 Hz, 1H), 7.36 (d, J=6.4 Hz, 2H), 7.04 (d, J=6.4 Hz, 2H), 6.89 (s, 1H), 6.68 (d, J=8.0 Hz, 1H), 5.20 (s, 1H), 1.68 (s, 9H), 0.74 (s, 9H); $^{19}$F NMR (376 MHz, $CDCl_3$): δ −60.42 (s, 3F); MS[FAB], m/z 925, [M+H]$^+$. The red crystals were confirmed to be Complex 6 having a chemical structure represented by

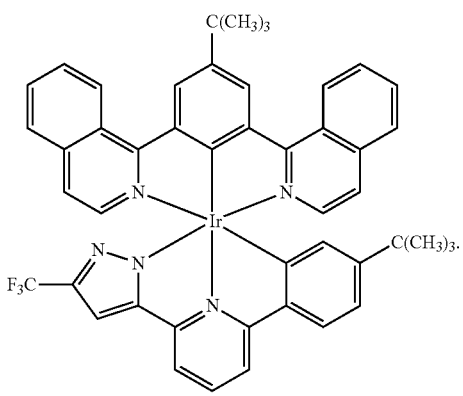

Preparation of organic light-emitting diodes (OLEDs 1~4)

Each of OLEDs 1~4 was prepared in a manner described below.

An anode substrate was prepared. The anode substrate included a glass substrate and an indium tin oxide (ITO) film formed on the glass substrate and having a sheet resistance of 10 ohm/square. The ITO film served as an anode of the OLED. The anode substrate was subjected to vibration cleaning by sequentially using an electronic grade cleaning agent, deionized water, acetone, and methanol. The anode substrate was dried using nitrogen gas and cleaned by UV-ozone to enhance a work function of the ITO film and cleanness of the anode substrate.

Subsequently, a hole transport layer, a light-emitting layer (including a guest material and a host material), an electron transport layer, an electron injection layer (made of lithium fluoride), and a cathode layer (made of aluminum) were sequentially deposited on the anode substrate at a rate of 0.2 nm/s under a pressure less than 10$^{-6}$ torr using a thermal evaporation device, to thereby obtain an organic light-emitting diode. The materials and thickness for the hole transport layer, the light-emitting layer, and the electron transport layer for each of OLEDs 1~4 are listed in Table 1.

TABLE 1

| | | OLED 1 | OLED 2 | OLED 3 | OLED 4 |
|---|---|---|---|---|---|
| Hole transport layer | Thickness material | 50 nm TmPyPB | 50 nm BP4mPy | 40 nm BP4mPy | 40 nm BP4mPy |
| Light emitting layer | Thickness | 30 nm | 30 nm | 30 nm | 30 nm |
| | Host material | mCP | mCP | mCP | mCP |
| | Guest material | Complex 2 | Complex 2 | Complex 4 | Complex 4 |
| | Conc. | 8 wt% | 8 wt% | 8 wt% | 8 wt% |
| Electron transport layer | Thickness of TAPC | 40 nm | 40 nm | 40 nm | 30 nm |
| | Thickness of TCTA | — | — | — | 10 nm |

* "—" means not included.
* TmPyPB: 1,3,5-tri[(3-pyridyl)-phen-3-yl]benzene
* BP4mPy: 3,3',5,5'-tetra[(m-pyridyl)-phen-3-yl]biphenyl
* mCP: 1,3-bis(N-carbazolyl)benzene
* TCTA: 4,4',4"-tris(N-carbazolyl)triphenylamine
* TAPC: 1,1-Bis[4-[N,N'-di(p-tolyl)amino]phenyl]cyclohexane

[Test Items for Complex]

Each of Complexes 1~6 obtained in Examples 1~6 was subjected to the following tests.

UV-Visible Spectrum

Each complex was dissolved in dichloromethane to prepare a test solution of a concentration of 10$^{-5}$ M. An absorption spectrum (ranging from 250 nm to 700 nm) of the test solution was measured using a UV-visible Spectrophotometer (Hitachi Spectrophotometer; Model no.: U-3900). A molar extinction coefficient (ε, M$^{-1}$cm$^{-1}$) of the complex was obtained accordingly. The UV/Vis spectra ($\lambda_{max}$) and the molar extinction coefficient (ε, M$^{-1}$ cm$^{-1}$) of Complexes 1~6 obtained in Examples 1 to 6 are listed in the following Table 2.

Fluorescence Spectrum

Each complex was dissolved in dichloromethane to prepare a test solution of a concentration of 10$^{-5}$ M. A fluorescence spectrum (ranging from 400 nm to 800 nm) of the test solution was measured using a fluorescence spectrophotometer (Edinburgh Instruments FLS920). The emission wavelengths of Complexes 1~6 obtained in Examples 1 to 6 are listed in the following Table 2.

Quantum Efficiency ($\Phi_{sol}$)

Each complex was dissolved in dichloromethane to prepare a test solution of a concentration of 10$^{-5}$ M. Quantum efficiency ($\Phi_{sol}$) of the test solution was measured using a fluorescence spectrophotometer (Edinburgh Instruments FLS920) at 20° C. and at an excitation wavelength of 350 nm. When measuring quantum efficiencies of Complexes 1, 2, 3, and 5, quinine, which has a quantum efficiency of 0.764 in ethanol, was used as a standard. When measuring quantum efficiencies of Complexes 4 and 6,4-(dicyanomethylene)-2-methyl-6-(4-dimethylaminostyryl)-4H-pyran, which has a quantum efficiency of 0.435 in ethanol, was used as a standard. The quantum efficiencies ($\Phi_{sol}$) of Complexes 1~6 obtained in Examples 1 to 6 are also listed in the following Table 2.

Emission Lifetime

Emission lifetime ($\tau_{obs}$) of each complex was measured using a photon counter in a fluorescence spectrophotometer (Edinburgh Instruments FLS920) with a hydrogen or nitrogen light as an excitation light. A nonradiative decay rate constant ($k_{nr}$) and a radiative decay rate constant ($k_r$) were calculated according to the following equations (1) and (2):

$$\phi_{sol.} = \frac{k_r}{k_r + k_{nr}} \quad (1)$$

$$\tau_{obs} = \frac{1}{k_r + k_{nr}} \quad (2)$$

The emission lifetime ($\tau_{obs}$), the nonradiative decay rate constant ($k_{nr}$), and the radiative decay rate constant ($k_r$) of each of Complexes 1~6 obtained in Examples 1 to 6 are also listed in the following Table 2.

[Testing for OLED]

Each of the OLEDs 1~4 was tested in a glove box. Power was applied to the OLED, and a driving voltage ($V_{on}$) was recorded by virtue of a current-voltage meter. A luminous intensity of the OLED was measured using photodiodes (United Detector Technology (UDT), model: PIN-10DP), and a maximum brightness ($L_{max}$) of the OLED was calculated. Electroluminescence of the OLED was measured using a spectrometer (OTO Photonics Inc., model: SD1200). The external quantum efficiency ($\eta_{ext}$), current efficiency ($\eta_c$), and power efficacy ($\eta_p$) of the OLED were calculated based on the above data. The CIE(x, y) coordinates of light emitted from the OLED were calculated from the spectral distribution of the light source and the CIE color-matching functions. The driving voltages ($V_{on}$), the maximum brightness ($L_{max}$), the external quantum efficiencies ($\eta_{ext}$), the current efficiencies ($\eta_c$), the power efficacies ($\eta_p$), and the x- and y-coordinate values of CIE(x, y) coordinates of the OLED at 100 cd/m² and 1000 cd/m² of the OLEDs 1~4 are listed in Table 3.

TABLE 2

| EX | UV/Vis spectra $\lambda_{max}$ (nm) ($\epsilon \times 10^{-4}$ M$^{-1}$cm$^{-1}$) | Fluorescence spectrum $\lambda_{max}$ (nm) | $\Phi_{sol}$ (%) | $\tau_{obs}$ (μs) | $k_r$ (×10⁵ s⁻¹) | $k_{nr}$ (×10⁵ s⁻¹) | Yield (%) |
|---|---|---|---|---|---|---|---|
| 1 | 281 (3.54), 373 (1.00), 395 (1.08), 464 (0.11) | 490, 526, 570 (sh) | 72 | 1.81 | 3.98 | 1.54 | 72 |
| 2 | 282 (3.66), 374 (1.14), 392 (1.25), 460 (0.12) | 493, 529, 571 (sh) | 64 | 3.37 | 1.90 | 1.07 | 56 |
| 3 | 284 (3.26), 397 0.75), 430 (0.80), 456 (0.61) | 505, 540 (sh) | 25 | 1.27 | 1.97 | 5.22 | 68 |
| 4 | 304 (2.09), 347 (1.12), 486 (0.83), 580 (0.08) | 594, 641 (sh) | 63 | 1.77 | 3.56 | 2.09 | 52 |
| 5 | 281 (4.43), 374 (0.83), 436 (0.88), 463 (0.67) | 515, 556 (sh) | 22 | 0.81 | 2.72 | 9.63 | 56 |
| 6 | 310 (2.60), 457 (0.85), 490 (1.05), 580 (0.11) | 602, 650 (sh) | 43 | 1.73 | 2.49 | 3.29 | 63 |

* $\Phi_{sol}$: Quantum efficiency
* $\tau_{obs}$: Emission lifetime
* $k_{nr}$: nonradiative decay rate constant
* $k_r$: radiative decay rate constant

TABLE 3

| OLED | | $\eta_{ext}$ (%) | $\eta_c$ (cd/A) | $\eta_p$ (lm/W) | $V_{on}$ (V) | CIE$_{[x,y]}$ 100 cd/m² | 1000 cd/m² | $L_{max}$ (cd/m²) |
|---|---|---|---|---|---|---|---|---|
| 1 | Peak | 13.2 | 41.4 | 35.5 | 3.8 | (0.305, 0.582) | (0.305, 0.580) | 15787 (11.0 V) |
|   | 100 cd/m² | 13.0 | 40.7 | 26.6 | | | | |
| 2 | Peak | 12.1 | 37.8 | 30.3 | 4.2 | (0.315, 0.576) | (0.315, 0.576) | 9696 (13.8 V) |
|   | 100 cd/m² | 10.5 | 32.9 | 16.7 | | | | |
| 3 | Peak | 14.7 | 21.8 | 21.9 | 3.7 | (0.628, 0.368) | (0.628, 0.370) | 24416 (13.4 V) |
|   | 100 cd/m² | 13.6 | 20.1 | 11.2 | | | | |
| 4 | Peak | 14.9 | 22.2 | 20.3 | 3.6 | (0.629, 0.368) | (0.628, 0.370) | 22740 (12.4 V) |
|   | 100 cd/m² | 13.7 | 20.4 | 20.3 | | | | |

* "Peak" means that the OLED was operated to have a maximum brightness.
* "100 cd/m²" means that the OLED was operated to have a brightness of 100 cd/m².
* $V_{on}$: Driving voltage
* $L_{max}$: Maximum brightness
* $\eta_{ext}$: External quantum efficiency
* $\eta_c$: Current efficiency
* $\eta_c$: Power efficacy It should be noted that Complexes 1~6 were synthesized in high yield (52%~72%). From the results shown in Tables 2 and 3, it can be found that Complexes 1~6 have good quantum efficiencies, and that OLEDs 1~4 provide good performance in terms of maximum brightness, external quantum efficiency, current efficiency and power efficacy.

While the disclosure has been described in connection with what is(are) considered the exemplary embodiment (s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A bis-tridentate iridium complex represented by a formula (I):

where:
$R^3$ to $R^8$ are each independently a hydrogen atom, a fluorine atom, an alkyl group, a perfluoroalkyl group, an alkoxy group, an aryl group, a dimethylamino group, a diphenylamino group, or a carbazolyl group;
$R^{21}$ to $R^{23}$ are each independently a hydrogen atom, a fluorine atom, an alkyl group, a perfluoroalkyl group, an alkoxy group, an aryl group, a dimethylamino group, a diphenylamino group, or a carbazolyl group, or $R^{21}$ and $R^{22}$ or $R^{22}$ and $R^{23}$ may be alkene groups joined to form a benzene ring which may be substituted by a fluorine atom, an alkyl group, a perfluoroalkyl group, an alkoxy group, an aryl group, a dimethylamino group, a diphenylamino group, or a carbazolyl group;

$R^9$ and $R^{10}$ are each independently a hydrogen atom, a fluorine atom, or an alkoxy group;

$X^1$ is a nitrogen atom or C—$X^{11}$, $X^{11}$ being a perfluoroalkyl group;

$X^2$ is a nitrogen atom or CH; and $X^3$ is a nitrogen atom or C—$X^{31}$, $X^{31}$ being a hydrogen atom, a fluorine atom, a cyano group, an alkyl group, a perfluoroalkyl group, an alkoxy group, or an aryl group.

2. The bis-tridentate iridium complex according to claim 1, wherein $X^1$ is C—$X^{11}$, $X^{11}$ being a perfluoroalkyl group.

3. The bis-tridentate iridium complex according to claim 2, wherein $X^2$ is CH.

4. The bis-tridentate iridium complex according to claim 3, wherein $R^3$, $R^4$, $R^5$, $R^6$, and $R^7$ are each a hydrogen atom, and $R^8$ is an alkyl group or a perfluoroalkyl group.

5. The bis-tridentate iridium complex according to claim 1, wherein $X^3$ is C—$X^{31}$, $X^{31}$ being a hydrogen atom, a fluorine atom, a cyano group, an alkyl group, a perfluoroalkyl group, an alkoxy group, or an aryl group.

6. The bis-tridentate iridium complex according to claim 5, wherein $X^{31}$ is a hydrogen atom, and $R^9$ and $R^{10}$ are each a fluorine atom.

7. The bis-tridentate iridium complex according to claim 5, wherein $X^{31}$ is an alkyl group, and $R^9$ and $R^{10}$ are each a hydrogen atom.

8. The bis-tridentate iridium complex according to claim 1, wherein $R^{21}$ to $R^{23}$ are each independently a hydrogen atom or an alkyl group.

9. The bis-tridentate iridium complex according to claim 1, wherein $R^{21}$ is a hydrogen atom or an alkyl group, and $R^{22}$ and $R^{23}$ are alkene groups joined to form a benzene ring.

10. The bis-tridentate iridium complex according to claim 1, which is represented by

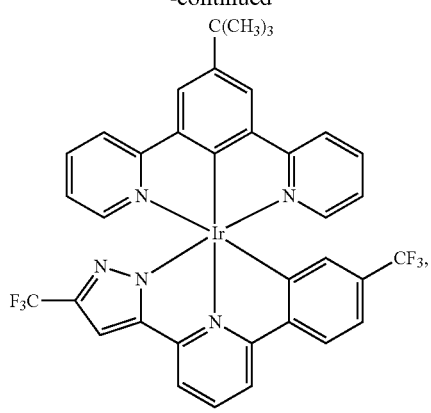

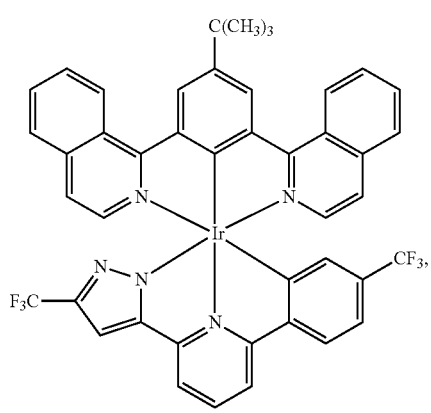

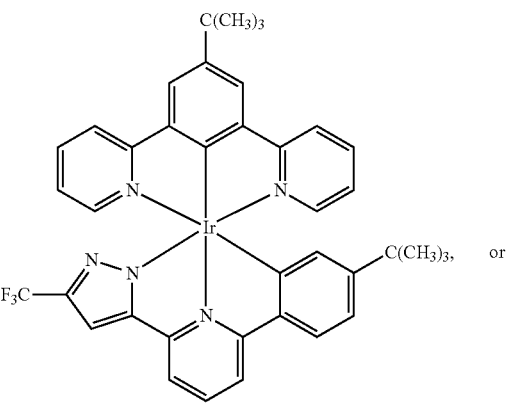

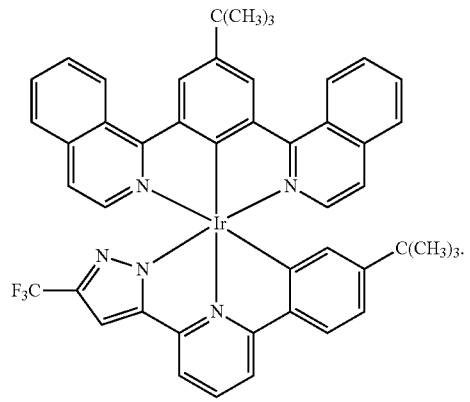

* * * * *